United States Patent [19]

Birkle

[11] Patent Number: 5,187,363
[45] Date of Patent: Feb. 16, 1993

[54] APPARATUS FOR DETECTING MINUTE QUANTITIES OF MOISTURE IN COOLANTS

[75] Inventor: Gebhard Birkle, Constance, Fed. Rep. of Germany

[73] Assignee: Bellino GmbH & Co., Göppingen, Fed. Rep. of Germany

[21] Appl. No.: 671,114

[22] Filed: Mar. 18, 1991

[30] Foreign Application Priority Data

Mar. 16, 1990 [DE] Fed. Rep. of Germany ....... 4008486

[51] Int. Cl.$^5$ .............................. H01J 5/16
[52] U.S. Cl. ................. 250/227.25; 73/29.04
[58] Field of Search ............ 250/231.1, 226, 227.25, 250/227.23; 73/73, 29.04, 29.05; 340/604; 62/126, 128

[56] References Cited

U.S. PATENT DOCUMENTS

| | | | |
|---|---|---|---|
| 3,039,355 | 6/1962 | Suter | 73/29.05 |
| 3,585,963 | 6/1971 | Hiszpanski | 73/29.04 |
| 4,634,856 | 1/1987 | Kirkham | 250/227.25 |
| 4,924,084 | 5/1990 | Lask et al. | 250/227.25 |

FOREIGN PATENT DOCUMENTS 666752 8/1988 Switzerland .
2129128 5/1984 United Kingdom .

*Primary Examiner*—David C. Nelms
*Attorney, Agent, or Firm*—Peter K. Kontler

[57] ABSTRACT

Apparatus for detecting minute quantities of moisture in a body of coolant has a support which confines a supply of particulate moisture sensitive material (such as $CoBr_2$ or $CoCl_2$) between a coolant-permeable filter and a light-transmitting seal. The coolant can contact the moisture sensitive material by way of the filter so that the material changes its color. A first diode serves to transmit light against the confined moisture sensitive material through the light-transmitting seal, and the incident light is reflected by the material to impinge upon a single generation diode which serves to transmit signals denoting the color of the moisture sensitive material to an evaluating circuit. The latter can activate an alarm system, interrupt the circulation of coolant and-/or otherwise influence the coolant when the percentage of moisture (normally in parts per million) in the coolant reaches a predetermined maximum permissible value.

30 Claims, 3 Drawing Sheets

APPARATUS FOR DETECTING MINUTE QUANTITIES OF MOISTURE IN COOLANTS

BACKGROUND OF THE INVENTION

The invention relates to moisture detecting apparatus in general, and more particularly to improvements in apparatus which can be used to detect minute quantities of moisture, such as in the ppm (parts per million) range. Still more particularly, the invention relates to improvements in apparatus which can be utilized with advantage for the determination of minute quantities of water in a coolant or refrigerant (hereinafter called coolant) which is circulated in the conditioning system of a motor vehicle, in the coolant conveying system of a refrigerator or in the coolant conveying system of another cooling machine.

It is well known that a circuit for a supply of coolant (e.g., Freon) which contains fluorohydrocarbons should not contain any moisture. At most, its water content can be in the parts per million range, namely well below a so-called critical water content range. If the coolant contains an excessive percentage of moisture, the moisture can exert an adverse influence upon the coolant and can lead to damage to, or even complete destruction of, the conditioning or refrigerating system. Therefore, it is necessary and customary to monitor the percentage of moisture in the circulating coolant. In accordance with heretofore known proposals, the monitoring is carried out optically by resorting to so-called indicator substances or materials which are contacted by coolant and the optical properties of which change as a result of contact with moisture in the coolant. Presently known indicator substances include cobalt bromide or cobaltous bromide ($CoBr_2$) and cobalt chloride or cobaltous chloride ($CoCl_2$). These indicator substances can be used with advantage to indicate the presence of minute quantities of water in Frigen 12 (Trademark) or in other types of coolants which contain fluorohydrocarbons. When the coolant which contacts an indicator substance consisting of or containing cobalt bromide or cobalt chloride carries minute quantities of moisture, the indicator substance undergoes a color change which is attributable to stepwise shifting of hydration water to thus induce a stepwise change of color of the metallic salt. Presently known proposals to ascertain the presence of minute quantities of moisture in coolant include the utilization of color indicators in the form of tablets containing cobalt bromide in or on a suitable substrate and being installed in the flow of coolant in such a way that the color of the tablet can be observed by a person looking through a window or the like. The relationship between the accumulation of hydration water and the changes of color is as follows:

$CoBr_2$ = green;
$CoBr_2 \times 1H_2O$ = blue;
$CoBr_2 \times 2H_2O$ = purple;
$CoBr_2 \times 6H_2O$ = pink.

Moisture detecting apparatus of the above outlined character are suitable for use in large or huge conditioning or refrigerating systems but are not suitable at all for installation in conditioning systems of motor vehicles and/or in cooling systems of refrigerators or other cooling machines. For example, the presence of water in a coolant-containing and conveying circuit can be attributable to a leak in the circuit, to diffusion, to dissociation or segregation and/or to splitting off and/or hydrolysis; this necessitates undertakings which can involve, for example, preventing the escape of coolant into the atmosphere or removing the moisture.

Published UK patent application No. GB 2 129 128 A of Hedges discloses a moisture detector which contains cobalt chloride and employs a radiation source in the form of a light emitting diode. Light which is emitted by the diode is reflected by cobalt chloride and is directed against a detector in the form of a photo transistor. A blue pass optical filter can be installed between the light emitting diode and the supply of cobalt chloride.

Swiss Pat. No. 666 752 to Gröninger discloses a relative humidity detector which employs a light source, a carrier of moisture-sensitive salts and a photoelectric element which serves to correlate the emission and absorption spectra in such a way that the maxima or absolute maxima in the spectral region of the carrier are located in the range of 400 to 900 nm and are spaced apart by not more than 200 nm. The light source, the carrier and the photoelectric element are installed in a housing containing a foil which is permeable to water vapors and contains dissolved moisture-sensitive salts. The foil is sealed in the housing and is exposed to light which issues from the light source. Slots in the housing enable atmospheric air to contact portions of the foil so that water molecules in the air can reach the salts in the foil by capillary action to initiate a color change. The patented apparatus is not intended for use, and cannot be installed, in conditioning or refrigeration systems.

OBJECTS OF THE INVENTION

An object of the invention is to provide an apparatus which can be utilized with particular advantage for detection of minute quantities of moisture (e.g., in the ppm range) in a stream, flow or stagnant body of coolant which is circulated or confined in a conditioning system for motor vehicles and/or in a cooling system which forms part of a refrigerator or another cooling machine.

Another object of the invention is to provide an apparatus for quantitative and qualitative detection of the presence of minute quantities of moisture in circulating or stagnant bodies of coolant in the conditioning systems of motor vehicles and/or in the cooling systems of refrigerators or other cooling machines.

A further object of the invention is to provide an apparatus which can be installed in existing conditioning systems and/or other cooling systems to detect minute quantities of moisture in the coolant.

An additional object of the invention is to provide an apparatus which is designed to generate signals for the actuation of alarms, for interruption of a conditioning or other cooling operation and/or for initiating other precautionary, preventive or remedial undertakings when the moisture content of the coolant reaches or exceeds a maximum permissible value.

Still another object of the invention is to provide a simple, compact and inexpensive apparatus which can utilize many standard components and can be used in new as well as in existing conditioning and/or other cooling systems.

A further object of the invention is to provide a novel and improved method of sealing certain parts of the apparatus from contact with circulating or stagnant coolant and moisture.

Another object of the invention is to provide novel and improved means for regulating the propagation of radiation toward and away from moisture sensitive material in the above outlined apparatus.

An additional object of the invention is to provide an apparatus which permits visual observation of the presence or absence of excessive amounts of moisture and is further capable of automatically signalling the presence of excessive quantities of moisture in a body of coolant, such as a coolant which contains fluorohydrocarbons.

SUMMARY OF THE INVENTION

The invention is embodied in an apparatus for detecting the presence of minute quantities of moisture (particularly in parts per million) in a body of coolant, particularly for ascertaining and indicating the presence of minute quantities of water in a flow of coolant in the conditioning system of a vehicle or refrigerator. The improved apparatus comprises a support or housing, a supply of moisture sensitive material (such as cobalt bromide or cobalt chloride) which is confined in the support and is continuously contactible by the body of coolant and the optical properties of which change as a result of contact with moisture-containing coolant, a source of radiation, means for directing radiation from the source upon the supply of moisture sensitive material so that the moisture sensitive material reflects the radiation and the characteristics of reflected radiation denote the optical properties of the moisture sensitive material, means for generating signals which denote the characteristics of reflected radiation, and means for evaluating the signals. The signal generating means can include means for generating electric signals, and the radiation source can include a source of light.

The support preferably includes a chamber for the supply of moisture sensitive material. The supply of moisture sensitive material is exposed to coolant at one side of the chamber, and a radiation transmitting member (e.g., a plate or disc of glass of plastic material) can be provided at another side of the chamber opposite the one side so that the radiation transmitting member is disposed between the moisture sensitive material on the one hand and the radiation source and the signal generating means on the other hand.

The radiation transmitting member can be installed in the support in such a way that it has a first surface confronting the supply of moisture sensitive material in the chamber and a second surface confronting the radiation source and the signal generating means. The second surface of the radiation transmitting member can be provided with a first optical element which forms part of the radiation directing means, and with a radiation-influencing second optical element serving to direct reflected radiation toward or directly against the signal generating means. At least one of the optical elements can constitute a radiation focusing lens, or at least one of the optical elements can constitute a radiation dispersing lens.

The support can include a first socket for the radiation transmitting member, for the supply of moisture sensitive material, for the radiation source, for the radiation directing means and for the signal generating means, and a second socket for entry of the body of coolant. A coolant-permeable wall (e.g., in the form of a filter or sieve) can be provided in the support between the two sockets, and the supply of moisture sensitive material is adjacent the respective side of the wall. The sockets can constitute coaxial bores or holes in the support, and the coolant-permeable wall can include a cupped or otherwise configurated receptacle for the supply of moisture sensitive material.

In accordance with a modification, that surface of the radiation transmitting member which confronts the supply of moisture sensitive material can be provided with a first radiation influencing element (e.g., a lens) which forms part of the radiation directing means, and with a second radiation influencing element (e.g., a lens) located in the path of radiation which is reflected from the supply of moisture sensitive material to the signal generating means. The two radiation influencing elements can be located in a recess which is provided in the respective surface of the radiation transmitting member, and such recess can form part of the aforementioned chamber, i.e., at least a portion of the supply of moisture sensitive material can be disposed in the recess.

The support can be designed in such a way that the radiation directing means and/or the signal generating means can be contacted by the body of coolant. Alternatively, a barrier (such as the aforementioned radiation transmitting member) can be installed in the support between the radiation directing and/or signal generating means on the one hand, and the body of coolant on the other hand.

The supply preferably consists of particulate solid moisture sensitive material at one side of the coolant-permeable wall which is located between such supply and the body of coolant. At least some particles of solid moisture sensitive material can constitute or resemble spheres, and the openings of the coolant-permeable wall are too small to permit passage of solid particulate moisture sensitive material.

The radiation source and/or the signal generating means can comprise a diode. Furthermore, the radiation source can include a source of infrared light.

The signal generating means can be positioned and designed to generate signals which denote the characteristics of radiation that is reflected by the supply of moisture sensitive material at an angle of less than 90°. Such signal generating means can be designed to generate binary signals (particularly light/dark signals) and/or to generate color-proportional electric signals and/or electric signals having a predetermined characteristic curve.

The support or housing can include or constitute a cartridge having a socket provided in one of its ends. The supply of moisture sensitive material is installed in the socket adjacent the coolant-permeable wall which is disposed between the supply and the body of coolant. The one end of the cartridge is preferably immersible into the body of coolant. The radiation transmitting member is installed in the socket between the supply of moisture sensitive material on the one hand and the radiation directing means and signal generating means on the other hand. The cartridge can include a larger diameter portion which is remote from the one end and a smaller-diameter portion which is provided with the socket and is insertable into the body of coolant so that the coolant can penetrate through the permeable wall to contact the moisture sensitive material.

The novel features which are considered as characteristic of the invention are set forth in particular in the appended claims. The improved moisture detecting apparatus itself, however, both as to its construction and its mode of operation, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
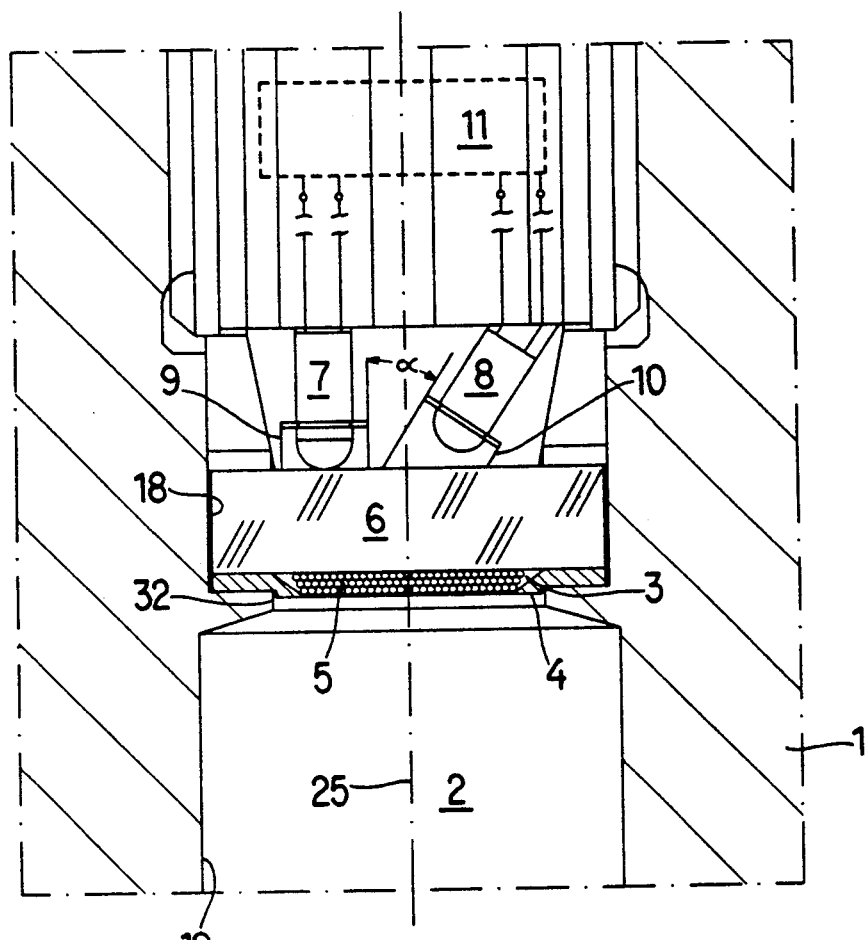
FIG. 1 is a fragmentary central sectional view of a moisture detecting apparatus which embodies one form of the invention, the of FIG. 1 being an enlarged view of a detail in the apparatus which is shown in FIG. 3.
Figure 3:
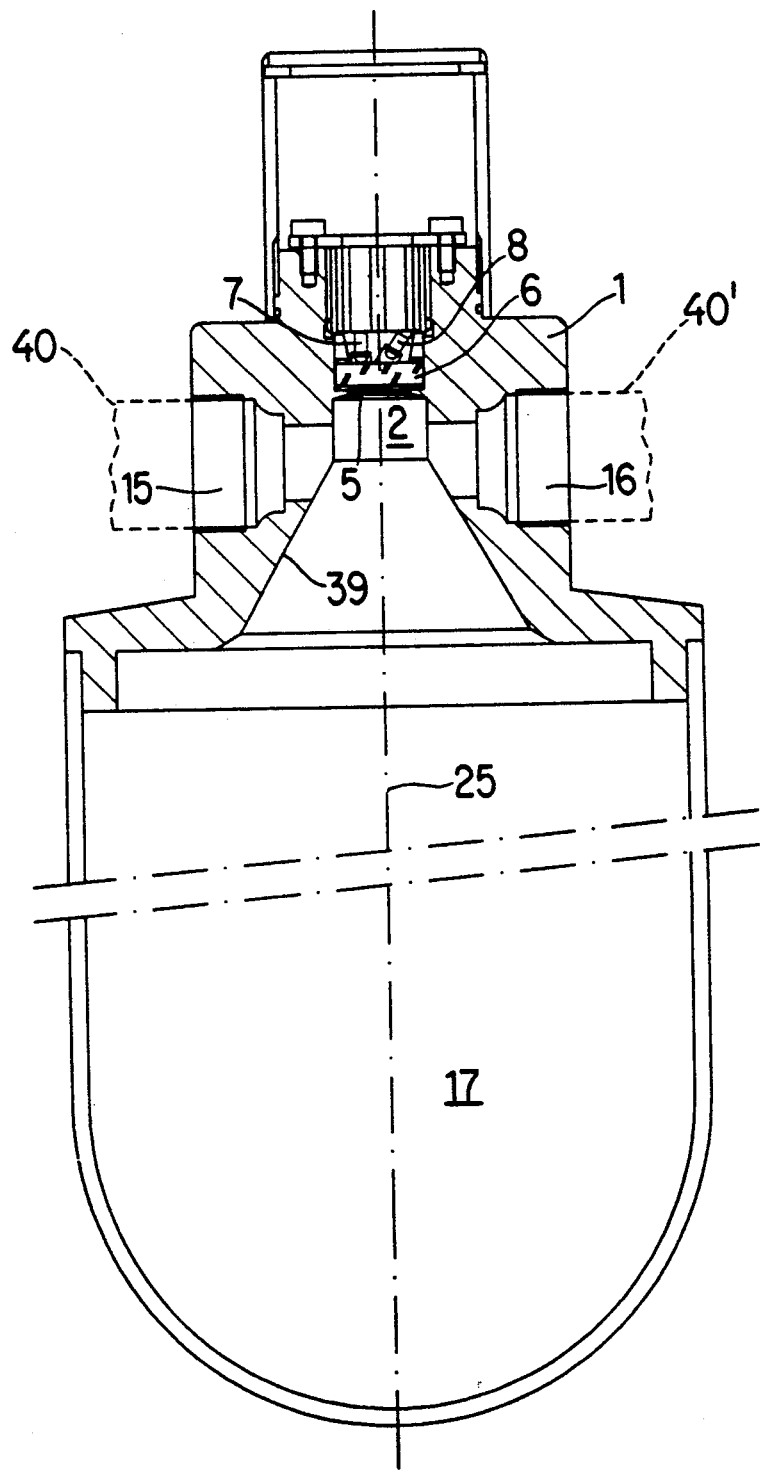
FIG. 3 is a fragmentary sectional view of the apparatus which embodies the structure of FIG. 1.

Referring first to FIGS. 1 and 3, there is shown an apparatus which can be utilized to detect the presence of minute quantities (particularly in parts per million) of moisture (water) in a flowing or circulating body of coolant, particularly in a coolant of the type used in the air conditioning systems of motor vehicles, in household refrigerators or other types of cooling systems. The apparatus comprises a support or housing 1 which can constitute a hollow cylinder having a central axis 25 and being provided with two sockets 18 and 19. The socket 18 is an axial bore or hole the innermost part of which constitutes a chamber 3 for a relatively small supply of solid particulate moisture sensitive material 5, e.g., spheres and/or granulate and or rods of cobalt bromide ($CoBr_2$) or cobalt (II) chloride ($CoCl_2$). The socket 19 also constitutes an axial bore or hole which extends to the chamber 3 and is accessible to or is filled with a body (e.g., a stream or flow) of coolant. Such coolant can contact and influence the supply of moisture sensitive material 5 by penetrating through the minute openings of a coolant-permeable wall 4 in the form of a cupped filter or sieve which is installed in the support 1 between the sockets 18, 19 and can receive at least the major portion of the supply of moisture sensitive material 5 (hereinafter called material for short) in the chamber 3. The rim of the cupped wall 4 rests on an internal collar 32 of the support 1; such collar is provided between the sockets 18 and 19 and reduces the area of that portion of the socket 19 which enables the coolant in the socket 19 to reach and to penetrate through the permeable central portion of the wall 4.

The rim of the permeable wall 4 abuts the adjacent side or surface of a radiation transmitting (preferably optically transparent) member 6 of glass or plastic material which overlies the material 5 in the chamber 3 of the socket 18 and separates such material from two diodes 7 and 8 in the socket 18. The member 6 resembles a disc and its peripheral surface is preferably in reliable sealing engagement with the surface surrounding the adjacent portion of the socket 18. Thus, coolant can penetrate from the socket 19 through the openings of the wall 4 and into contact with the material 5 in the chamber 3 but such coolant cannot penetrate beyond the member 6 to contact the diode 7 and/or 8. The member 6 can be said to constitute a barrier between the body of coolant in the socket 19 and the diodes 7, 8 in the socket 18. The arrangement may be such that the coolant is in continuous contact with the material 5 or contacts the material 5 at regular or irregular intervals. At any rate, the permeable wall 4 ensures that the material 5 is continuously contactible by the body of coolant in the socket 19.

The diode 7 constitutes a combined radiation source and means for directing radiation through the member 6 and against the material 5 so that the radiation is reflected by material 5 and is directed against the diode 8 which constitutes a signal generating device. The illustrated diode 7 is designed to emit infrared light, and the orientation of the diodes 7, 8 relative to each other is such that the diode 8 responds to radiation which has been reflected through an angle alpha of not more than 90°. The diodes 7 and 8 are respectively mounted in holders 9 and 10 both adjacent that side or surface of the radiation transmitting member 6 which faces away from the material 5 in the chamber 3. It is presently preferred to employ a diode 7 which emits light in the visible range of the spectrum, and the diode 8 is designed to process reflected visible light by generating electric signals which denote the characteristics of reflected radiation, i.e., the changed optical properties of the material 5 when the latter is contacted by moisture in the body of coolant. Since the temperature of the body of coolant is likely to be low or even extremely low, it is often desirable to employ a diode 7 which emits infrared light, particularly to emit light in the near infrared region.

The diodes 7 and 8 are connected to an electric circuit 11 which is or can be installed in the socket 18 and serves to evaluate electric signals from the diode 8 as well as to start the diodes when it is desired to proceed with the detection of moisture in the body of coolant.

The space 2 in the socket 19 of the support 1 can be completely or partially filled with a body of coolant, and this space extends all the way to the respective side of the permeable wall 4. The space 2 can receive a stream or flow of coolant by way of an inlet 15 in the support 1, and the latter has an outlet 16 for evacuation of coolant from the space 2. A conduit 40 delivers coolant to the inlet 15, and a conduit 40' receives coolant from the outlet 16. The lower portion 39 of the socket 19 (as viewed in FIG. 3) is enlarged to resemble a funnel, and the support 1 can be mounted on a vessel 17 which contains a relatively large supply of coolant. The means for circulating the coolant so as to establish a flow from the conduit 40 into the space 2 and thence into the conduit 40' is or can be of conventional design and is not shown in the drawing.

The operation is as follows:

A stream or flow of coolant is circulated through the space 2 in the socket 19 of the housing in a direction from the inlet 15 toward the outlet 16. The arrangement may be such that the coolant is caused to circulate along an endless path as is customary in many types of conditioning systems for use in motor vehicles. The coolant is free to penetrate through the pores and/or otherwise configurated openings of the wall 4 and to contact the particles of solid moisture sensitive material in the chamber 3. The particles can resemble or constitute irregularly shaped granulate, spheres, rods or the like. All of the particles which constitute the material 5 may but need not be of identical size and/or shape, as long as they cannot escape through the openings of the wall 4 and into the coolant in the space 2. The particles of material 5 are preferably small or very small so that the overall coolant-contacting surface of the material 5 is very large.

The diode 7 emits radiation (light) which penetrates through the radiation transmitting member 6 and impinges upon the material 5 to be reflected at the angle alpha toward and against the diode 8. Reflected radiation penetrates through the member 6 which seals the material 5 from the diodes 7 and 8. Signals which are generated by the diode 8 are transmitted to the evaluating circuit 11. If the color of the material 5 changes as a result of contact with moisture in the coolant, the spectrum of reflected radiation changes accordingly and the diode transmits to the evaluating circuit a signal which is indicative of the presence of moisture in the coolant. The circuit 11 then generates a signal which can be used to generate an alarm and/or to initiate other preventive, remedial, safety or security measures.

The intensity or another characteristic of the electric signal which is generated by the diode 8 can be proportional to the extent of color change of the material 5, i.e., to the percentage of moisture in the coolant which has contacted the material 5 in the chamber 3. Alternatively, the intensity or another characteristic of the electric signal can vary in accordance with a characteristic curve which need not be proportional and is a qualitative and quantitative indicator of moisture content in the monitored body of coolant.

If it is desired to achieve a mere quantitative determination of moisture content of a coolant in a conditioning or other cooling system, the characteristic curve is replaced with a binary effect in the form of a light/dark signal. This can be achieved by optical filtering of the reflected or non-reflected radiation beam or beams by resorting to suitable filter means. Such monitoring renders it possible to simplify the design of the evaluating circuit 11.

Figure 2:
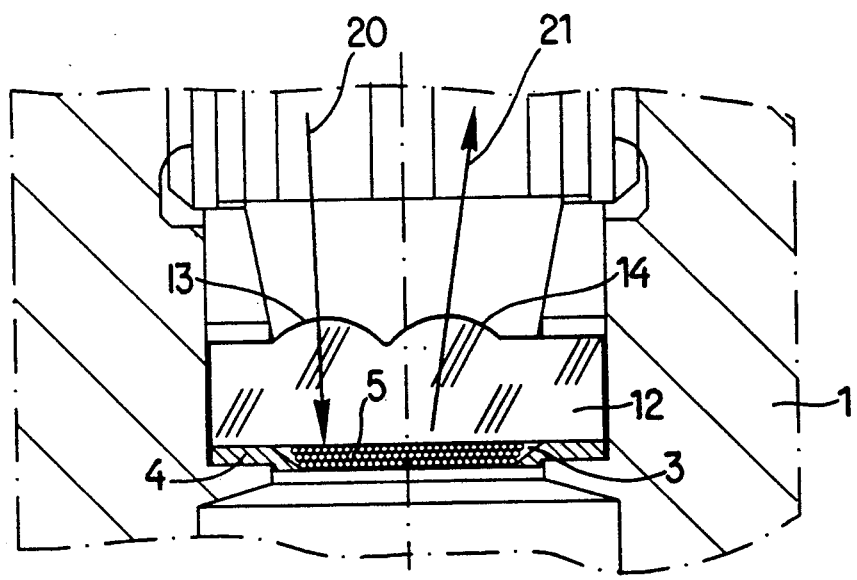
FIG. 2 is a fragmentary central sectional view of a modified moisture detecting apparatus wherein a radiation transmitting member is installed between the supply of moisture sensitive material and the radiation source and has optical elements confronting the radiation source and the signal generating means.

FIG. 2 shows a modified radiation transmitting member 12 one side or surface of which sealingly engages the rim of the permeable wall 4 in the chamber 3 for the material 5. The other side or surface of the member 12 is provided with two optical elements 13 and 14 in the form of lenses. The lens 13 serves to direct radiation from the diode 7 (not shown) or another radiation source toward the material 5, and the lens 14 serves to direct reflected radiation toward the diode 8 (not shown) or another signal generating device. The member 12 can be made of transparent glass or transparent plastic material. The lens 13 can be designed to focus or to disperse radiation (denoted by the arrow 20) which is emitted by the radiation source, and the lens 14 serves to focus or disperse reflected radiation (denoted by the arrow 21) which propagates itself from the material 5 toward the signal generating means.

Figures 4A, 4B:
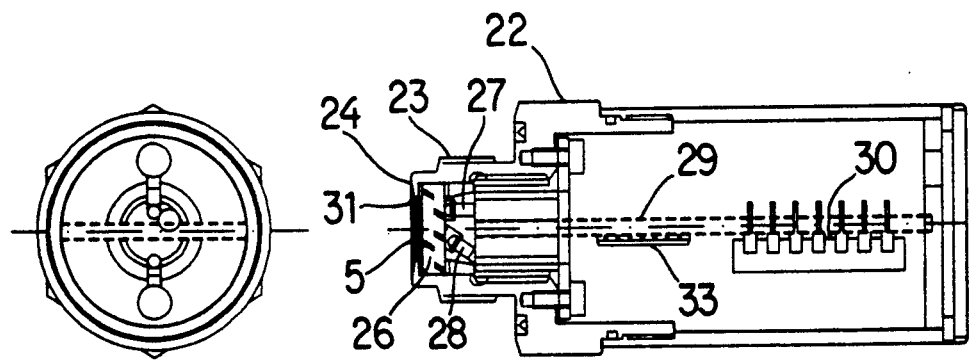
FIG. 4a is a schematic sectional view of a third apparatus wherein the support includes a cartridge.
FIG. 4b is an end elevational view of the apparatus which is shown in FIG. 4.

FIGS. 4 and 4a illustrate a third apparatus wherein the housing or support resembles or constitutes a preferably cylindrical cartridge 22. The cartridge 22 is preferably designed as part of a miniaturized apparatus for installation in existing conditioning or refrigerating systems. The tubular smaller-diameter portion 23 at one end of the cartridge 22 has a socket 31 the open end of which contains a coolant-permeable wall 24 (e.g., a filter or sieve) which enables the coolant to contact a moisture sensitive material 5 in the socket 31. The material 5 is confined between the wall 24 and a radiation transmitting member 26 (e.g., a disc of transparent glass or plastic material) which separates the material 5 from two diodes 27, 28 constituting functional equivalents of the diodes 7 and 8. The openings of the wall 24 permit coolant and moisture to penetrate into contact with the material 5 but the granular, spherical and/or otherwise configurated solid particles of the material 5 are incapable of escaping from the socket 31. The evaluating circuit in the larger-diameter portion of the support 22 includes a conductor 29 (e.g., a circuit board) and electrical or electronic components 30, 33. These components can be mounted on the circuit board 29. The latter can extend all the way to the smaller-diameter portion 23 so that it can serve as a holder for the diode 27 and-/or 28.

The smaller-diameter portion 23 of the cartridge 22 can be provided with an external thread which can be moved into mesh with the thread in a tapped bore or hole in a conduit or vessel (not shown) for a body of coolant which is circulated in the conditioning system of a vehicle (e.g., an automobile) or in the cooling system of a refrigerator or another cooling machine.

Figure 5:
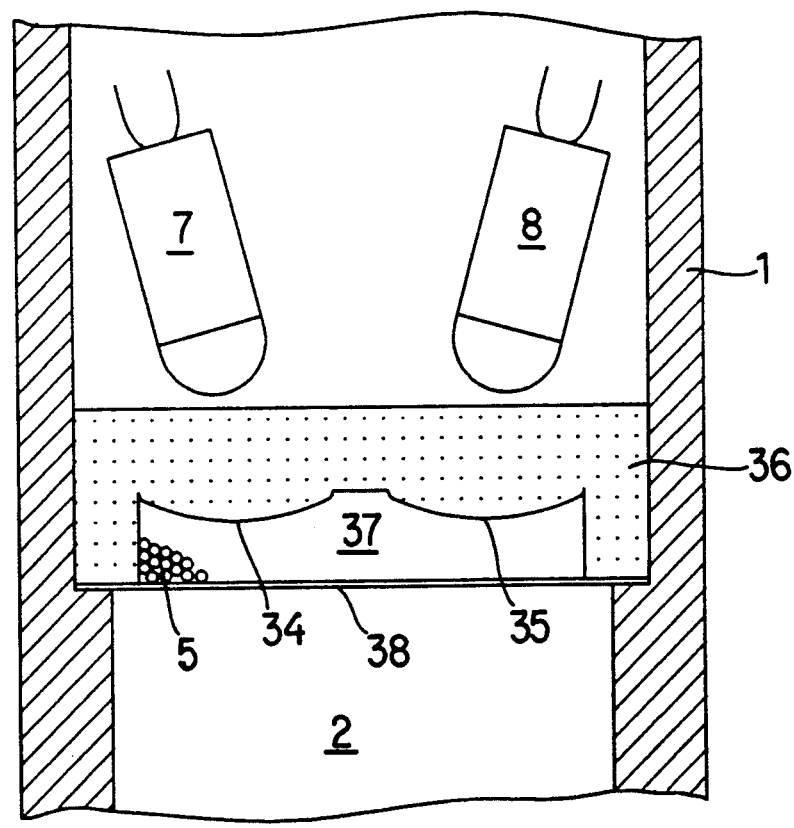
FIG. 5 is a fragmentary sectional view of a fourth apparatus which constitutes a modification of the apparatus of FIG. 2.

FIG. 5 illustrates a portion of a further moisture detecting apparatus which differs from the apparatus of FIG. 2 in that the radiation transmitting member 36 has a flat outer side or surface confronting the diodes 7 and 8 and a second side or surface which confronts the space 2 and is provided with a recess 37 forming part of or constituting a chamber for the supply of moisture sensitive material 5. The material is confined in the recess 37 by a coolant-permeable wall 38 which overlies an internal shoulder of the support 1 and permits coolant to penetrate through its openings into contact with the granulate, rods, spheres and/or otherwise configurated solid particles of the material 5. The inner side of the member 36 is further provided with two optical elements in the form of lenses 34, 35 which are located in the recess 37. The element 34 directs radiation from the diode 7 against the material 5, and the element 35 directs reflected radiation from the material 5 toward the radiation-sensitive surface of the diode 8. The member 36 can be made of pressed or molded glass or of compression molded plastic material, the same as the member 6 and/or 12 and/or 26.

An important advantage of the improved apparatus is its sensitivity. Thus, the apparatus can readily detect minute quantities (in the ppm range) of moisture in a flowing or stagnant body of coolant because the moisture sensitive material is confined in such a way that it is continuously contactible by the body of coolant. Furthermore, the apparatus can automatically signal the presence of excessive quantities of moisture in a body of coolant so that it is not necessary to rely on sporadic or continuous visual monitoring of the color of moisture sensitive material. The moisture dependent changes of color of the moisture sensitive material are such that the apparatus can indicate qualitative as well as quantitative changes of moisture content in the body of coolant. The sensitivity of the apparatus can be readily selected in such a way that the diode 8 or 28 or another suitable signal generating device can generate an electric signal when the moisture content of monitored coolant reaches a low or extremely low threshold value to thus permit the carrying out of precautionary undertakings even before the moisture content of the coolant reaches an unacceptable value. As mentioned above, the electric signals which are generated by the signal generating device can be evaluated and processed to actuate an alarm, to turn on a safety device, to interrupt the circulation or other flow of the coolant and/or to furnish visual indications of the moisture content.

Another important advantage of the improved apparatus is that its operation is practically errorless. This is due to the utilization of a radiation emitting device and a signal generating device as a means for facilitating determination of color changes of the material 5. The transmission of signals from the signal generating device to the evaluating circuit renders it possible to dispense with actual visual determination of the moisture content. The quality and reliability of visual observation depends on the conscientiousness of the person in charge, on the ability of the person in charge to discriminate between different colors and different color shades, on the extent and nature of illumination of the location for visual determination of the color of the material 5 and/or on certain other factors all of which can be disregarded when the determination of color changes is automated by resorting to a radiation source, to means for directing radiation upon the material 5, to means for generating electric signals, and to means for evaluating and processing the signals.

The apparatus of FIGS. 4 and 4a exhibits the advantage that it can be fitted into existing coolant-containing or conveying circuits at a minimal cost. All that is necessary is to provide a location for insertion of the tubular portion 23 of the cartridge 22 into a pipeline or into a vessel in such a way that the confined coolant can reach the supply of moisture sensitive material without the need for any gates, valves or other flow controlling devices. At the present time, the portion 23 is preferably provided with external threads to mate with the internal threads in the tapped bore of a pipeline or a vessel, or with internal threads to accept the externally threaded portion of a nipple or a like outlet for coolant on a pipeline or on a vessel for a supply of stagnant or flowing coolant. A thus mounted cartridge-like support 22 does not influence the flow of coolant and prevents uncontrolled escape of the coolant.

The improved moisture detecting apparatus can be modified in a number of additional ways without departing from the spirit of the invention. Thus, and though it is presently preferred to install the radiation emitting and/or the signal generating means in such a way that they cannot be contacted by the body of coolant, it is equally possible to install the diode 7 or 27 and/or the diode 8 or 28 in or in contact with the body of coolant. In the latter instance, the radiation source and/or the signal generating means is connected with an externally mounted evaluating circuit by conductor means which are properly insulated from the coolant and from moisture. In certain instances, the installation of radiation emitting and/or signal generating means in or in contact with the body of coolant simplifies the sealing of the coolant from the surrounding atmosphere.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for detecting the presence of minute quantities of moisture in a body of coolant, particularly for ascertaining and indicating the presence of minute quantities of water in a flow of coolant in a conditioning system, comprising a support; a supply of moisture sensitive material, said supply being confined in said support and being continuously contactible by the body of coolant and the optical properties of said material changing as a result of contact with coolant containing minute quantities of moisture; a source of radiation; means for directing radiation from said source upon the supply of moisture sensitive material so that the moisture sensitive material reflects the radiation and the characteristics of reflected radiation denote the optical properties of moisture sensitive material; means for generating signals denoting the characteristics of reflected radiation; and means for evaluating said signals.

2. The apparatus of claim 1, wherein said signal generating means includes means for generating electric signals.

3. The apparatus of claim 1, wherein said radiation source includes a source of light.

4. The apparatus of claim 1, wherein said support includes a chamber for the supply of moisture sensitive material, said chamber having a first side at which the supply of moisture sensitive material therein is exposed to coolant and a second side, and further comprising a radiation transmitting member disposed at the second side of said chamber between said supply of moisture sensitive material and said radiation source.

5. The apparatus of claim 4, wherein said radiation transmitting member is disposed between said supply of moisture sensitive material and said signal generating means.

6. The apparatus of claim 5, wherein said radiation transmitting member contains glass.

7. The apparatus of claim 5, wherein said radiation transmitting member contains a plastic material.

8. The apparatus of claim 4, wherein said radiation transmitting member has a first surface confronting the supply of moisture sensitive material in said chamber, a second surface confronting said radiation source and said signal generating means, a first optical element provided at said second surface and forming part of said radiation directing means, and a radiation influencing second optical element provided at said second surface to direct reflected radiation toward said signal generating means.

9. The apparatus of claim 8, wherein at least one of said optical elements includes a radiation focusing lens.

10. The apparatus of claim 8, wherein at least one of said optical elements includes a radiation dispersing lens.

11. The apparatus of claim 4, wherein said support includes (a) a first socket for said radiation transmitting member, said supply of moisture sensitive material, said radiation source, said radiation directing means and said signal generating means, and (b) a second socket for the body of coolant, and further comprising a coolant-permeable wall provided in said support between said sockets, said supply of moisture sensitive material being adjacent said wall.

12. The apparatus of claim 11, wherein said sockets are coaxial bores or holes in said support.

13. The apparatus of claim 11, wherein said wall includes a cupped receptacle for the supply of moisture sensitive material.

14. The apparatus of claim 4, wherein said radiation transmitting member has a first surface confronting the supply of moisture sensitive material, a second surface confronting said radiation source and said signal generating means, a first radiation influencing element provided at said second surface and forming part of said radiation directing means, and a second radiation influencing optical element provided at said second surface in the path of radiation which is reflected from the supply of moisture sensitive material to said signal generating means.

15. The apparatus of claim 14, wherein said first surface has a recess and said optical elements are disposed in said recess.

16. The apparatus of claim 15, wherein said recess forms part of said chamber and at least a portion of the supply of moisture sensitive material is disposed in said recess.

17. The apparatus of claim 1, wherein said radiation source and/or said signal generating means is contactible by the body of coolant.

18. The apparatus of claim 1, further comprising a barrier between said radiation directing means and/or said signal generating means on the one hand and the body of coolant on the other hand.

19. The apparatus of claim 1, wherein said supply consists of particulate solid moisture sensitive material, and further comprising a coolant-permeable wall provided in said support between said supply and the body of coolant.

20. The apparatus of claim 19, wherein said supply includes substantially spherical solid moisture sensitive material and said wall has openings which are too small to permit passage of solid particulate moisture sensitive material.

21. The apparatus of claim 1, wherein said radiation source and/or said signal generating means includes a diode.

22. The apparatus of claim 21, wherein said radiation source includes a source of infrared light.

23. The apparatus of claim 1, wherein said signal generating means is positioned to generate signals denoting the characteristics of radiation which is reflected by said supply of moisture sensitive material at an angle of less than 90°.

24. The apparatus of claim 1, wherein the moisture sensitive material is selected from the group consisting of cobalt bromide and cobalt chloride.

25. The apparatus of claim 1, wherein said signal generating means includes means for generating binary signals, particularly light/dark signals.

26. The apparatus of claim 1, wherein said signal generating means includes means for generating color-proportional electric signals.

27. The apparatus of claim 1, wherein said signal generating means includes means for generating electric signals having a predetermined characteristic curve.

28. The apparatus of claim 1, wherein said support includes a cartridge having a first end and a second end, and a socket provided in one of said ends, said supply of moisture sensitive material being provided in said socket and further comprising a coolant-permeable wall disposed between the supply of moisture sensitive material in said socket and the body of coolant, said one end of said cartridge being immersible into the body of coolant.

29. The apparatus of claim 28, further comprising a radiation transmitting member provided in said socket between said supply of moisture sensitive material on the one hand and said radiation directing means and signal generating means on the other hand.

30. The apparatus of claim 29, wherein said cartridge comprises a larger-diameter portion including the other of said ends and a smaller-diameter portion insertable into the body of coolant and including said one end and said chamber.

* * * * *